(12) United States Patent
Altshuler et al.

(10) Patent No.: US 7,351,252 B2
(45) Date of Patent: Apr. 1, 2008

(54) METHOD AND APPARATUS FOR PHOTOTHERMAL TREATMENT OF TISSUE AT DEPTH

(75) Inventors: Gregory B. Altshuler, Wilmington, MA (US); Andrei V. Erofeev, North Andover, MA (US); Henry H. Zenzie, Dover, MA (US); R. Rox Anderson, Lexington, MA (US); Dieter Manstein, Boston, MA (US); James Burke, III, Londonderry, NH (US); Andrew Radl, Dunbarton, NH (US); Michael Z. Smirnov, St. Petersburg (RU)

(73) Assignee: Palomar Medical Technologies, Inc., Burlington, MA (US)

( * ) Notice: Subject to any disclaimer, the term of this patent is extended or adjusted under 35 U.S.C. 154(b) by 324 days.

(21) Appl. No.: 10/465,137

(22) Filed: Jun. 19, 2003

(65) Prior Publication Data

US 2004/0093042 A1 May 13, 2004

Related U.S. Application Data

(60) Provisional application No. 60/389,871, filed on Jun. 19, 2002.

(51) Int. Cl.
*A61N 5/06* (2006.01)
(52) U.S. Cl. ............... 607/88; 607/89; 606/3; 606/9
(58) Field of Classification Search ............ 607/88–92; 606/3–29
See application file for complete search history.

(56) References Cited

U.S. PATENT DOCUMENTS

| | | | |
|---|---|---|---|
| 1,706,161 A | 3/1929 | Hollnagel | |
| 2,472,385 A | 6/1949 | Rollman | |
| 3,327,712 A | 6/1967 | Kaufman et al. | |
| 3,486,070 A | 12/1969 | Engel | |
| 3,527,932 A | 9/1970 | Thomas | |
| 3,538,919 A | 11/1970 | Meyer | |
| 3,622,743 A | 11/1971 | Muncheryan | |

(Continued)

FOREIGN PATENT DOCUMENTS

| | | |
|---|---|---|
| AT | 400305 B | 4/1995 |
| AT | 400305 | 12/1995 |
| AU | 1851583 A | 3/1984 |
| DE | 3837248 A1 | 5/1990 |
| DE | 9102407 | 7/1991 |

(Continued)

OTHER PUBLICATIONS

Ohshiro et al., "The Ruby and Argon Lasers in the Treatment of the Naevi," Annals Academy of Medicine, Apr. 1983, vol. 12, No. 2, pp. 388-395.

(Continued)

*Primary Examiner*—A. Farah
(74) *Attorney, Agent, or Firm*—Thomas J. Engellenner; Deborah A. Miller; Nutter McClennen & Fish, LLP

(57) ABSTRACT

The present invention provides method and apparatus for treating tissue in a region at depth by applying optical radiation thereto of a wavelength able to reach the depth of the region and of a selected relatively low power for a duration sufficient for the radiation to effect the desired treatment while concurrently cooling tissue above the selected region to protect such tissue. Treatment may be enhanced by applying mechanical, acoustic or electrical stimulation to the region.

47 Claims, 5 Drawing Sheets

U.S. PATENT DOCUMENTS

| | | |
|---|---|---|
| 3,693,623 A | 9/1972 | Harte et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,900,034 A | 8/1975 | Katz et al. |
| 4,233,493 A | 11/1980 | Nath |
| 4,273,109 A | 6/1981 | Enderby |
| 4,275,335 A | 6/1981 | Ishida |
| 4,316,467 A | 2/1982 | Muckerheide |
| 4,388,924 A | 6/1983 | Weissman et al. |
| 4,456,872 A | 6/1984 | Froeschle |
| 4,461,294 A | 7/1984 | Baron |
| 4,524,289 A | 6/1985 | Hammond et al. |
| 4,539,987 A * | 9/1985 | Nath et al. ............... 606/3 |
| 4,561,440 A | 12/1985 | Kubo et al. |
| 4,591,762 A | 5/1986 | Nakamura |
| 4,608,978 A | 9/1986 | Rohr |
| 4,617,926 A | 10/1986 | Sutton |
| 4,695,697 A | 9/1987 | Kosa |
| 4,718,416 A | 1/1988 | Nanaumi |
| 4,733,660 A | 3/1988 | Itzkan |
| 4,745,909 A | 5/1988 | Pelton et al. |
| 4,747,660 A | 5/1988 | Nishioka et al. |
| 4,749,913 A | 6/1988 | Stuermer et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,884,560 A | 12/1989 | Kuracina |
| 4,905,690 A | 3/1990 | Ohshiro et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,127,395 A | 7/1992 | Bontemps |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,267,399 A | 12/1993 | Johnston |
| 5,282,797 A | 2/1994 | Chess |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A * | 9/1994 | Ghaffari ............... 606/9 |
| 5,344,434 A | 9/1994 | Talmore |
| 5,348,551 A | 9/1994 | Spears et al. |
| 5,350,376 A | 9/1994 | Brown |
| 5,358,503 A | 10/1994 | Bertwell et al. |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,425,754 A * | 6/1995 | Braun et al. ............. 607/88 |
| 5,458,140 A | 10/1995 | Eppstein et al. |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles |
| 5,531,739 A | 7/1996 | Trelles |
| 5,531,740 A | 7/1996 | Black |
| 5,549,660 A | 8/1996 | Mendes et al. |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,655,547 A | 8/1997 | Karni |
| 5,658,323 A | 8/1997 | Miller |
| 5,660,836 A | 8/1997 | Knowlton |
| 5,662,643 A | 9/1997 | Kung et al. |
| 5,662,644 A | 9/1997 | Swor |
| 5,683,380 A | 11/1997 | Eckhouse et al. |
| 5,698,866 A | 12/1997 | Doiron et al. |
| 5,707,403 A | 1/1998 | Grove et al. |
| 5,720,772 A * | 2/1998 | Eckhouse ............... 607/88 |
| 5,722,397 A | 3/1998 | Eppstein |
| 5,735,844 A * | 4/1998 | Anderson et al. ............... 606/9 |
| 5,735,884 A | 4/1998 | Thompson et al. |
| 5,742,392 A | 4/1998 | Anderson et al. |
| 5,743,901 A | 4/1998 | Grove et al. |
| 5,755,751 A | 5/1998 | Eckhouse |
| 5,759,200 A | 6/1998 | Azar |
| 5,769,076 A | 6/1998 | Mackawa et al. |
| 5,782,249 A | 7/1998 | Weber et al. |
| 5,810,801 A | 9/1998 | Anderson et al. |
| 5,814,008 A | 9/1998 | Chen et al. |
| 5,814,040 A * | 9/1998 | Nelson et al. ............... 606/9 |
| 5,814,041 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,827,264 A | 10/1998 | Hohla |
| 5,828,803 A | 10/1998 | Eckhouse |
| 5,830,208 A * | 11/1998 | Muller ............... 606/9 |
| 5,836,877 A | 11/1998 | Zavislan |
| 5,836,999 A | 11/1998 | Eckhouse et al. |
| 5,840,048 A | 11/1998 | Cheng |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,871,480 A | 2/1999 | Tankovich |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,913,883 A | 6/1999 | Alexander et al. |
| 5,916,211 A | 6/1999 | Quon et al. |
| 5,944,748 A | 8/1999 | Mager et al. |
| 5,948,011 A | 9/1999 | Knowlton |
| 5,949,222 A | 9/1999 | Buono |
| 5,954,710 A | 9/1999 | Paolini et al. |
| 5,955,490 A | 9/1999 | Kennedy et al. |
| 5,964,749 A | 10/1999 | Eckhouse et al. |
| 5,968,033 A | 10/1999 | Fuller |
| 5,968,034 A | 10/1999 | Fullmer et al. |
| 5,977,723 A | 11/1999 | Yoon |
| 5,984,915 A | 11/1999 | Loeb et al. |

| Patent/Pub No. | Date | Inventor |
|---|---|---|
| 6,015,404 A | 1/2000 | Altshuler et al. |
| 6,022,316 A | 2/2000 | Epstein et al. |
| 6,026,828 A | 2/2000 | Altshuler |
| 6,027,495 A | 2/2000 | Miller |
| 6,030,399 A | 2/2000 | Ignotz et al. |
| 6,032,071 A | 2/2000 | Binder |
| RE36,634 E | 3/2000 | Ghaffari |
| 6,036,684 A | 3/2000 | Tankovich et al. |
| 6,050,990 A | 4/2000 | Tankovich et al. |
| D424,197 S | 5/2000 | Sydlowski et al. |
| 6,056,738 A | 5/2000 | Marchitto et al. |
| 6,059,820 A | 5/2000 | Baronov |
| 6,074,382 A | 6/2000 | Asah et al. |
| 6,080,146 A | 6/2000 | Altshuler et al. |
| 6,086,580 A | 7/2000 | Mordon et al. |
| 6,096,029 A | 8/2000 | O'Donnell, Jr. |
| 6,096,209 A | 8/2000 | O'Brien et al. |
| 6,104,959 A | 8/2000 | Spertell |
| 6,117,129 A | 9/2000 | Mukai |
| 6,120,497 A | 9/2000 | Anderson |
| 6,142,939 A | 11/2000 | Eppstein et al. |
| 6,149,644 A | 11/2000 | Xie |
| 6,162,211 A | 12/2000 | Tankovich et al. |
| 6,162,212 A | 12/2000 | Kreindel et al. |
| 6,173,202 B1 | 1/2001 | Eppstein et al. |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,197,020 B1 | 3/2001 | O'Donnell |
| 6,210,425 B1 | 4/2001 | Chen |
| 6,214,034 B1 | 4/2001 | Azar |
| 6,228,075 B1 | 5/2001 | Furumoto |
| 6,229,831 B1 | 5/2001 | Nightingale et al. |
| 6,235,016 B1 | 5/2001 | Stewart |
| 6,236,891 B1 | 5/2001 | Ingle et al. |
| 6,245,093 B1 | 6/2001 | Li et al. |
| 6,263,233 B1 | 7/2001 | Zavislan et al. |
| 6,264,649 B1 | 7/2001 | Whitcroft et al. |
| 6,267,780 B1 | 7/2001 | Streeter |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,283,956 B1 | 9/2001 | McDaniel |
| 6,290,713 B1 | 9/2001 | Russell |
| 6,306,130 B1 | 10/2001 | Anderson et al. |
| 6,319,274 B1 | 11/2001 | Shadduck |
| 6,340,495 B1 | 1/2002 | Sumian et al. |
| 6,350,276 B1 | 2/2002 | Knowlton |
| 6,354,370 B1 | 3/2002 | Miller et al. |
| 6,358,272 B1 | 3/2002 | Wilden |
| 6,383,177 B1 | 5/2002 | Balle-Petersen et al. |
| 6,387,089 B1 | 5/2002 | Kreindel et al. |
| 6,402,739 B1 | 6/2002 | Neev |
| 6,406,474 B1 | 6/2002 | Neuberger et al. |
| 6,424,852 B1 | 7/2002 | Zavislan |
| 6,425,912 B1 | 7/2002 | Knowlton |
| 6,436,094 B1 | 8/2002 | Reuter |
| 6,461,296 B1 | 10/2002 | Desai |
| 6,471,712 B2 | 10/2002 | Burres |
| 6,471,716 B1 | 10/2002 | Pecukonis |
| 6,475,211 B2 | 11/2002 | Chess et al. |
| 6,494,900 B1 | 12/2002 | Salansky et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,530,915 B1 | 3/2003 | Eppstein et al. |
| 6,537,270 B1 | 3/2003 | Elbrecht et al. |
| 6,558,372 B1 | 5/2003 | Altshuler |
| 6,572,637 B1 | 6/2003 | Yamazaki et al. |
| 6,602,245 B1 | 8/2003 | Thiberg |
| 6,605,080 B1 * | 8/2003 | Altshuler et al. ............... 606/3 |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,600 B1 | 11/2003 | Kohler |
| 6,648,904 B2 | 11/2003 | Altshuler et al. |
| 6,653,618 B2 | 11/2003 | Zenzie |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,676,654 B1 | 1/2004 | Balle-Petersen et al. |
| 6,679,837 B2 | 1/2004 | Daikuzono |
| 6,685,699 B1 | 2/2004 | Eppstein et al. |
| 6,689,124 B1 | 2/2004 | Thiberg |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,743,222 B2 | 6/2004 | Durkin et al. |
| 6,770,069 B1 | 8/2004 | Hobart et al. |
| 6,790,205 B1 | 9/2004 | Yamazaki et al. |
| 6,808,532 B2 | 10/2004 | Andersen et al. |
| RE38,670 E | 12/2004 | Asah et al. |
| 6,863,781 B2 * | 3/2005 | Nocera et al. ......... 204/157.52 |
| 6,878,144 B2 | 4/2005 | Altshuler et al. |
| 6,888,319 B2 | 5/2005 | Inochkin et al. |
| 6,902,563 B2 * | 6/2005 | Wilkens et al. ................ 606/9 |
| 2001/0041886 A1 | 11/2001 | Durkin et al. |
| 2002/0005475 A1 | 1/2002 | Zenzie |
| 2002/0026225 A1 | 2/2002 | Segal |
| 2002/0091377 A1 | 7/2002 | Anderson |
| 2002/0123745 A1 | 9/2002 | Svaasand et al. |
| 2002/0128635 A1 | 9/2002 | Atshuler et al. |
| 2002/0161357 A1 | 10/2002 | Anderson |
| 2002/0173780 A1 | 11/2002 | Atshuler et al. |
| 2003/0004499 A1 | 1/2003 | McDaniel |
| 2003/0023283 A1 | 1/2003 | McDaniel |
| 2003/0032900 A1 | 2/2003 | Ella |
| 2003/0032950 A1 | 2/2003 | Atshuler et al. |
| 2003/0036680 A1 | 2/2003 | Black |
| 2003/0055414 A1 | 3/2003 | Altshuler et al. |
| 2003/0057875 A1 | 3/2003 | Inochkin et al. |
| 2003/0065314 A1 | 4/2003 | Altshuler et al. |
| 2003/0100936 A1 | 5/2003 | Altshuler et al. |
| 2003/0109787 A1 | 6/2003 | Black |
| 2003/0109860 A1 | 6/2003 | Black |
| 2003/0129154 A1 | 7/2003 | McDaniel |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0232303 A1 | 12/2003 | Black |
| 2004/0006332 A1 | 1/2004 | Black |
| 2004/0010298 A1 | 1/2004 | Altshuler et al. |
| 2004/0015156 A1 | 1/2004 | Vasily |
| 2004/0024388 A1 | 2/2004 | Altshuler |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0093042 A1 | 5/2004 | Altshuler et al. |
| 2004/0133251 A1 | 7/2004 | Altshuler et al. |
| 2004/0147984 A1 | 7/2004 | Altshuler et al. |
| 2004/0162549 A1 | 8/2004 | Altshuler et al. |
| 2004/0162596 A1 | 8/2004 | Altshuler et al. |
| 2004/0191729 A1 | 9/2004 | Altshuler et al. |
| 2004/0193235 A1 | 9/2004 | Altshuler et al. |
| 2004/0193236 A1 | 9/2004 | Altshuler et al. |
| 2004/0199227 A1 | 10/2004 | Altshuler et al. |

| | | | |
|---|---|---|---|
| 2004/0204745 A1 | 10/2004 | Altshuler et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2005/0038418 A1 | 2/2005 | Altshuler et al. |
| 2005/0049582 A1 | 3/2005 | DeBenedictis et al. |
| 2005/0049658 A1 | 3/2005 | Connors et al. |
| 2005/0107849 A1 | 5/2005 | Altshuler et al. |

FOREIGN PATENT DOCUMENTS

| | | |
|---|---|---|
| EP | 0142671 A1 | 5/1985 |
| EP | 0565331 A2 | 10/1993 |
| EP | 0598984 A1 | 6/1994 |
| EP | 0724894 A2 | 8/1996 |
| EP | 0726083 A2 | 8/1996 |
| EP | 0736308 A2 | 10/1996 |
| EP | 0755698 A2 | 1/1997 |
| EP | 0763371 A2 | 3/1997 |
| EP | 0765673 A2 | 4/1997 |
| EP | 0765674 A2 | 4/1997 |
| EP | 0783904 A2 | 7/1997 |
| EP | 0884066 | 12/1998 |
| EP | 0885629 | 12/1998 |
| EP | 1038505 A2 | 9/2000 |
| EP | 1138349 | 10/2001 |
| EP | 1147785 | 10/2001 |
| EP | 1219258 A1 | 7/2002 |
| EP | 1226787 | 7/2002 |
| EP | 1457234 A2 | 9/2004 |
| FR | 2199453 | 4/1974 |
| FR | 2591902 | 6/1987 |
| GB | 2044908 A | 10/1980 |
| GB | 2123287 A | 2/1984 |
| GB | 2356570 | 5/2001 |
| GB | 2360946 A | 10/2001 |
| GB | 2368020 | 4/2002 |
| GB | 2390021 | 12/2003 |
| GB | 2397528 | 7/2004 |
| JP | 2001145520 | 5/2001 |
| JP | 2003192809 | 2/2005 |
| RU | 2082337 C1 | 6/1997 |
| RU | 2089126 C1 | 10/1997 |
| RU | 2089127 C1 | 10/1997 |
| RU | 2096051 C1 | 11/1997 |
| RU | 2122848 C1 | 10/1998 |
| WO | WO 86/02783 | 5/1986 |
| WO | WO 90/00420 | 1/1990 |
| WO | WO 92/16338 | 1/1992 |
| WO | WO 92/19165 | 11/1992 |
| WO | WO 93/05920 | 4/1993 |
| WO | WO 95/15725 | 6/1995 |
| WO | WO 95/32441 | 11/1995 |
| WO | WO 96/23447 | 8/1996 |
| WO | WO 96/25979 | 8/1996 |
| WO | WO 96/36396 | 11/1996 |
| WO | WO 96/41579 | 12/1996 |
| WO | WO 97/13458 | 4/1997 |
| WO | WO 98/04317 | 2/1998 |
| WO | WO 98/24507 | 6/1998 |
| WO | WO 98/51235 | 11/1998 |
| WO | WO 98/52481 | 11/1998 |
| WO | WO 99/17666 | 4/1999 |
| WO | WO 99/17667 | 4/1999 |
| WO | WO 99/27997 A1 | 6/1999 |
| WO | WO 99/29243 | 6/1999 |
| WO | WO 99/38569 | 8/1999 |
| WO | WO 99/46005 | 9/1999 |
| WO | WO 99/49937 A1 | 10/1999 |
| WO | WO 00/02491 | 1/2000 |
| WO | WO 00/03257 | 1/2000 |
| WO | WO 00/32272 | 6/2000 |
| WO | WO 00/40266 | 7/2000 |
| WO | WO 00/43070 | 7/2000 |
| WO | WO 00/64537 | 11/2000 |
| WO | WO 00/71045 A1 | 11/2000 |
| WO | WO 00/74781 A1 | 12/2000 |
| WO | WO 00/78242 A1 | 12/2000 |
| WO | WO 01/03257 A1 | 1/2001 |
| WO | WO 01/26573 | 4/2001 |
| WO | WO 01/34048 A1 | 5/2001 |
| WO | WO 01/42671 A1 | 6/2001 |
| WO | WO 01/54606 A1 | 8/2001 |
| WO | WO 01/54770 | 8/2001 |
| WO | WO 02/53050 A1 | 7/2002 |
| WO | WO 02/094116 A1 | 11/2002 |
| WO | WO 2004/073537 | 9/2004 |
| WO | WO 2004/084752 | 10/2004 |
| WO | WO 2004/086947 A2 | 10/2004 |
| WO | WO 2005/007003 A1 | 1/2005 |

OTHER PUBLICATIONS

Sumian, C.C. et al., "A Preliminary Clinical And Histopathological Study Of Laser Skin Resurfacing Using A Frequency-Doubled Nd:YAG Laser After Application of Chromofilm®," Journal of Cutaneous Laser Therapy, vol. 1, pp. 159-166, 1999.

Sumian, C.C. et al., "Laser Skin Resurfacing Using A Frequency Doubled Nd:YAG Laser After Topical Application Of An Exogenous Chromophore," Lasers in Surgery and Medicine, vol. 25, pp. 43-50, 1999.

G.B. Altshuler et al., "Acoustic response of hard dental tissues to pulsed laser action," SPIE, vol. 2080, Dental Application of Lasers, pp. 97-103, 1993.

G.B. Altshuler et al., "Extended theory of selective photothermolysis," Lasers in Surgery and Medicine, vol. 29, pp. 416-432, 2001.

R.L. Amy & R. Storb, "Selective mitochondrial damage by a ruby laser microbeam: An electron microscopic study," Science, vol. 15, pp. 756-758, Nov. 1965.

R.R. Anderson et al., "The optics of human skin," Journal of Investigative Dermatology, vol. 77, No. 1, pp. 13-19, 1981.

R.R. Anderson & J.A. Parrish, "Selective photothermolysis: Precise microsurgery by selective absorption of pulsed radiation," Science, vol. 220, pp. 524-527, Apr. 1983.

A.V. Belikov et al. "Identification of enamel and dentine under tooth laser treatment," SPIE vol. 2623, Progress in Biomedical Optics Europe Series, Proceedings of Medical Applications of Lasers III, pp. 109-116, Sep. 1995.

Altea Therapeutics—Medicines Made Better (single page website print-out), printout date Sep. 30, 2004.

Doukas et al., "Transdermal Drug Delivery With a Pressure Wave," Advanced Drug Delivery Reviews 56 (2004), pp. 559-579.

P. Bjerring et al., "Selective Non-Ablative Wrinkle Reduction by Laser," J Cutan Laser Ther, vol. 2, pp. 9-15, 2000.

J.S. Dover et al., "Pigmented guinea pig skin irradiated with Q-switched ruby laser pulses," Arch Dermatol, vol. 125, pp. 43-49, Jan. 1989.

L.H. Finkelstein & L.M. Blatstein, "Epilation of hair-bearing urethral grafts using the neodymium:yag surgical laser," Journal of Urology, vol. 146, pp. 840-842, Sep. 1991.

L. Goldman, Biomedical Aspects of the Laser, Springer-Verlag New York Inc., publishers, Chapts. 1, 2, & 23, 1967.

L. Goldman, "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

L. Goldman, "Effects of new laser systems on the skin," Arch Dermatol., vol. 108, pp. 385-390, Sep. 1973.

L. Goldman, "Laser surgery for skin cancer," New York State Journal of Medicine, pp. 1897-1900, Oct. 1977.

L. Goldman, "Surgery by laser for malignant melanoma," J. Dermatol. Surg. Oncol., vol. 5, No. 2, pp. 141-144, Feb. 1979.

L. Goldman, "The skin," Arch Environ Health, vol. 18, pp. 434-436, Mar. 1969.

L. Goldman & D.F. Richfield, "The effect of repeated exposures to laser beams," Acta derm.-vernereol., vol. 44, pp. 264-268, 1964.

L. Goldman & R.J. Rockwell, "Laser action at the cellular level," JAMA, vol. 198, No. 6, pp. 641-644, Nov. 1966.

L. Goldman & R.G. Wilson, "Treatment of basal cell epithelioma by laser radiation," JAMA, vol. 189, No. 10, pp. 773-775.

L. Goldman et al., "The biomedical aspects of lasers," JAMA, vol. 188, No. 3, pp. 302-306, Apr. 1964.

L. Goldman et al., "Effect of the laser beam on the skin, Preliminary report" Journal of Investigative Dermatology, vol. 40, pp. 121-122, 1963.

L. Goldman et al., "Effect of the laser beam on the skin, III. Exposure of cytological preparations," Journal of Investigative Dermatology, vol. 42, pp. 247-251, 1964.

L. Goldman et al., "Impact of the laser on nevi and melanomas," Archives of Dermatology, vol. 90, pp. 71-75, Jul. 1964.

L. Goldman et al., "Laser treatment of tattoos, A preliminary survey of three year's clinical experience," JAMA, vol. 201, No. 11, pp. 841-844, Sep. 1967.

L. Goldman et al., "Long-term laser exposure of a senile freckle," ArchEnviron Health, vol. 22, pp. 401-403, Mar. 1971.

L. Goldman et al., "Pathology, Pathology of the effect of the laser beam on the skin," Nature, vol. 197, No. 4870, pp. 912-914, Mar. 1963.

L. Goldman et al., "Preliminary investigation of fat embolization from pulsed ruby laser impacts of bone," Nature, vol. 221, pp. 361-363, Jan. 1969.

L. Goldman et al. "Radiation from a Q-switched ruby laser, Effect of repeated impacts of power output of 10 megawatts on a tattoo of man," Journal of Investigative Dermatology, vol. 44, pp. 69-71, 1965.

L. Goldman et al., "Replica microscopy and scanning electron microscopy of laser impacts on the skin," Journal of Investigative Dermatology, vol. 52, No. 1, pp. 18-24, 1969.

M.C. Grossman et al., "Damage to hair follicles by normal-mode ruby laser pulses," Journal of he American Academy of Dermatology, vol. 35, No. 6, pp. 889-894, Dec. 1996.

E. Klein et al., "Biological effects of laser radiation 1.," Northeast Electroncis Research and Engineering Meeting, NEREM Record, IEEE catalogue No. F-60, pp. 108-109, 1965.

J.G. Kuhns et al., "Laser injury in skin," Laboratory Investigation, vol. 17, No. 1, pp. 1-13, Jul. 1967.

J.G. Kuhns et al., "Biological effects of laser radiation II Effects of laser irradiation on the skin," NEREM Record, pp. 152-153, 1965.

R.J. Margolis et al., "Visible action spectrum for melanin-specific selective photothermolysis," Lasers in Surgery and Medicine, vol. 9, pp. 389-397, 1989.

J.A. Parrish, "Selective thermal effects with pulsed irradiation from lasers: From organ to organelle," Journal of Investigative Dermatology, vol. 80, No. 6 Supplement, pp. 75s-80s, 1983.

T. Shimbashi & T. Kojima, "Ruby laser treatment of pigmented skin lesions," Aesth. Plast. Surg., vol. 19, pp. 225-229, 1995.

Stratton, K., et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

C.R. Taylor et al., "Treatment of tattoos by Q-switched ruby laser," Arch. Dermatol. vol. 126, pp. 893-899, Jul. 1990.

V.V. Tuchin, "Laser light scattering in biomedical diagnostics and therapy," Journal of Laser Applications, vol. 5, No. 2-3, pp. 43-60, 1993.

S. Watanabe et al, "Comparative studies of femtosecond to microsecond laser pulses on selective pigmented cell injury in skin," Photochemistry and Photobiology, vol. 53, No. 6, pp. 757-762, 1991.

A.J. Welch et al., "Evaluation of cooling techniques for the protection of the pidermis during HD-yag laser irradiation of the skin," Neodymium-Yag Laser in Medicine and Surgery, Elsevier Science Publishing Co., publisher, pp. 195-204, 1983.

R.B. Yules et al., "The effect of Q-switched ruby laser radiation on dermal tattoo pigment in man," Arch Surg, vol. 95, pp. 179-180, Aug. 1967.

E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1-18, 1971.

Abstracts Nos. 17-19, Lasers in Surgery and Medicine, ASLMS, Supplement 13, 2001.

* cited by examiner

METHOD AND APPARATUS FOR PHOTOTHERMAL TREATMENT OF TISSUE AT DEPTH

CROSS-REFERENCE TO RELATED APPLICATION

This invention claims the benefit of now abandoned U.S. Provisional Patent Application Serial No. 60/389,871, filed Jun. 19, 2002, entitled "Method and Apparatus for Subdermal Heating," by G. Altshuler, et al., incorporated herein by reference in its entirety.

BACKGROUND

1. Field of the Invention

This invention relates to methods and apparatus for the photothermal treatment of tissue and, more particularly, to methods and apparatus for photothermal treatment of at least a selected region of tissue located starting at a depth at about the boundary zone of dermal and subdermal tissue and extending therebelow.

2. Description of the Related Art

The benefits of being able to raise and/or lower the temperature in a selected region of tissue for various therapeutic and cosmetic purposes has been known for some time. For instance, heated pads or plates or various forms of electromagnetic radiation, including microwave radiation, electricity, infrared radiation and ultrasound have previously been used for heating subdermal muscles, ligaments, bones and the like to, for example, increase blood flow, to otherwise promote the healing of various injuries and other damage, and for various therapeutic purposes, such as frostbite or hyperthermia treatment, treatment of poor blood circulation, physical therapy, stimulation of collagen, cellulite treatment, adrenergic stimulation, wound healing, psoriasis treatment, body reshaping, non-invasive wrinkle removal, etc. The heating of tissues has also been utilized as a potential treatment for removing cancers or other undesired growths, infections and the like. Heating may be applied over a small localized area, over a larger area, for example to the hands or feet, or over larger regions of tissue, including the entire body.

Since most of the techniques described above involve applying energy to tissue at depth through the patient's skin surface, peak temperature generally occurs at or near the patient's skin surface and decrease, sometimes significantly, with depth. Further, while microwaves or ultrasonic and other acoustic radiation have been used in the past for certain heating treatments at depth, as disclosed in, for example, U.S. Pat. No. 5,871,524 to Knowlton, U.S. Pat. No. 5,769,879 to Richards, et al., U.S. Pat. No. 5,507,790 to Weiss, or U.S. Pat. No. 5,143,063 to Feliner, since such radiation, particularly microwaves, are potentially mutagenic and can otherwise result in cell or systemic damage and, particularly for acoustic sources, are relatively expensive, and may not be practical for large-area treatment, these techniques have had limited use for the heating of tissues.

While optical and near infrared (NIR) radiation (collectively referred to hereinafter as "optical radiation" is generally both less expensive and, being non-mutagenic, safer than microwaves radiation, the use of optical radiation has heretofore not been considered suitable for most applications involving heating of tissue at depth, the term "tissue at depth" as used herein meaning tissue at the border zone of the dermis and hypodermis, some of which tissue may be in the lower dermis, mostly at a depth deeper than 1 mm, and tissue below this border zone to a depth of up to about 50 mm The reason why this radiation has not been considered suitable is because such radiation is both highly scattered and highly absorbed in surface layers of tissue, precluding significant portions of such radiation from reaching the tissue regions at depth to cause heating thereof. In view of the energy losses due to scattering and absorption, substantial optical (including NIR) energy must be applied in order for enough such energy to reach a region of tissues at depth to have a desired effect. However, such high energy can cause damage to the surface layers of tissue, making it difficult to achieve desired photothermal treatments in tissue regions at depth. For these reasons, optical radiation has heretofore had at most limited value for therapeutic and cosmetic treatments on tissue at depth.

Further, while heating of tissue at depth alone is useful for many treatments, there are treatments, for example to relieve pain and stiffness in muscles or joints, where heating in conjunction with massage or other mechanical stimulation, ultrasound or other acoustic stimulation or electrical stimulation of the tissue may also be useful.

Thus, a need exists for improved method and apparatus for photothermal treatment of tissue regions at depth, and in particular for treatment of subdermal regions of tissue, and for method and apparatus for combining heating with stimulation in such regions for various treatments.

SUMMARY OF THE INVENTION

The present invention generally relates to methods and apparatus for photothermal treatment, both therapeutic and cosmetic, of tissue located at depth in a patient's body, as this tern has previously been defined. Optical radiation utilized in practicing the invention is at a wavelength or wavelength band which is neither highly scattered in the patient's skin nor highly absorbed by water in tissue so that the maximum quantity of such radiation can reach the treatment region at depth. The wavelength utilized typically is between about 600 nm and about 1850 nm, more preferably between about 800 nm and about 1350 nm, and most preferably between about 1050 nm and about 1250 nm. Other potential ranges for certain depths of tissue are set forth in Table 1. The longer the wavelength, the lower the scattering; however, outside of the indicated bands, water absorption is so high that little radiation can reach tissue at depth. While the tissue to be treated may be a chromophore at the wavelength(s) utilized within the above bands, this is not a limitation on the invention, and absorption by water, and to a lesser extent fat or lipid, in the region is generally sufficient to achieve the desired heating. In some applications, absorption at certain wavelengths can be increased by delivering a suitable chromophore to the treatment region. The optical radiation source utilized may be a monochromatic source, such as a laser or light emitting diode (LED), or may be a wide spectrum source such as a halogen lamp or arc lamp. Where a wide spectrum source is used, filtering or shifting of wavelengths outside the above bands may be performed. The source may also be a pulsed source or a continuous wave (CW) source. Natural light sources such the sun can also be used to practice this invention. Where the source is a pulsed source, the source typically remains over a treatment region for the duration of each pulse, or a train of pulses may be applied. Where the source is a (CW) source, it is typically moved over the surface of the patients skin at a selected rate, the rate of movement determining the dwell time over a given treatment region.

The invention also requires that cooling be applied to the patient's skin surface concurrently with the application of optical radiation thereto. While the radiation reaches the tissue at depth to be treated quickly to begin the heating thereof, cooling propagates as a cold wave protecting tissue above the treatment region and moving the depth of maximum heating further into the skin. Ideally the cooling wave propagates to a depth just above the treatment region, but does not extend to the treatment region at least until sufficient energy has been delivered to the treatment region to effect the desired treatment. Cooling may also be applied to the patient's skin prior to the application of radiation thereto to more effectively protect tissue above the treatment region and to more rapidly result in maximum heat being at or near the desired depth. This may also permit higher energy and shorter duration for the radiation source. The head used to apply the radiation may also be used to apply cooling.

Another feature of the invention is that the radiation is applied at low power for an extended time, the time varying with the depth of treatment and with the treatment being performed. For example, the time may vary from approximately 2 seconds to approximately 2 hours for depths of approximately 1 mm to 50 mm respectively. Depending on depth, the treatment being performed and other factors, the power density may vary from approximately 0.2 to 50 W/cm2, more preferably from approximately 0.5 to 20 W/cm2, and most preferably from 0.5 to 10 W/cm2 or 0.5 to 5 W/cm2.

Other advantages, novel features, and objects of the invention will become apparent from the following detailed description of the invention when considered in conjunction with the accompanying drawings, which are schematic and which are not intended to be drawn to scale. In the figures, each identical, or substantially similar component that is illustrated in various figures is represented by a single numeral or notation. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

Non-limiting embodiments of the present invention will be described by way of example with reference to the accompanying drawings in which.

DETAILED DESCRIPTION

Figure 1:
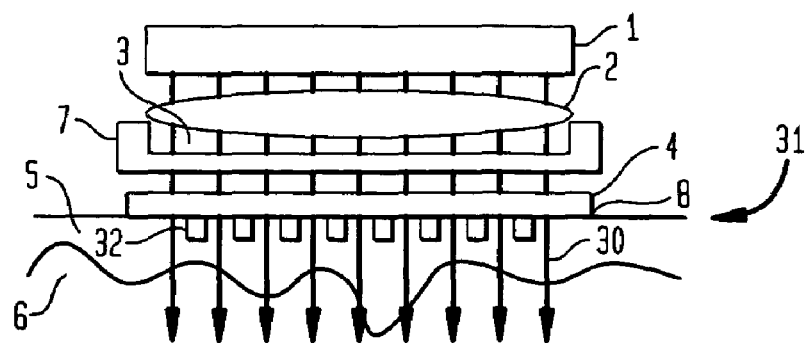
FIG. 1 is a schematic diagram of one embodiment of the invention, as applied to a tissue sample.

Applications in which the invention may be useful include the treatment of various diseases, particularly, cellulite and subcutaneous fat treatment, physical therapy, muscle and skeletal treatments, including relief of pain and stiffness for muscles and joints, and treatment of spinal cord problems, and treatment of cumulative trauma disorders (CTD's) such as carpel tunnel syndrome (CTS), tendonitis and bursitis, fibromyalgia, lymphedema and cancer therapy.

More specifically with respect to cancer therapy, hyperthermia resulting from utilizing the teachings of this invention may be utilized to treat various skin cancers including, but not limited to, basel cell carcinoma, squamous cell carcinoma, lymphoma and possibly treatment (palliative) of melanoma. Hyperthermia may also enhance the efficacy of radiation, for example x-ray, therapy, chemotherapy, therapy with immunmodulators such as ALDARA or PDT therapy. Such combination therapy may for example reduce required treatment time.

The tissue to be treated may be a collagen-rich tissue. Collagen-rich tissues that may be treated include superficial cortical bone, synovium joint capsules, tendon sheaths, menisci, myofascial interfaces, periosteum, fibrotic muscle, or major nerve trunks. The device may also be used for reshaping procedures such as non-invasive wrinkle removal through stimulation of collagen production in a subsurface region of tissue. Heating of the subsurface region of tissue to a temperature of between 37.5 and 45° C. may stimulate generation of new collagen and/or elastin. For example, expression of HSP70 ("Heat Shock Protein") may be stimulated when the tissue is heated to between 41 and 42° C. for between 20 and 30 minutes. Other proteins, cytokins and/or growth factors may also be stimulated or released in response to heating. Significant new collagen deposition, formation or rearrangement may be possible, which may improve skin appearance or texture, allowing wrinkles, fine lines, scars, stretch marks or other indicators to be removed. In general, there exists a relation between the temperature reached and the time of application that is necessary to stimulate new collagen deposition and prevent irreversible damage. Additionally, multiple treatments may be used in some treatment modalities.

Hypothermia resulting from utilizing the teachings of this invention may also be utilized for hair growth management, and for treatment of psoriasis, scars, rosacea and various conditions of toe and finger nails. For hair growth management, which includes temporary and permanent hair removal and control of hair growth, a dermal or subdermal temperature rise of a few degrees, for example to 42-45° C. can produce an anagen effluvium. This could be particularly useful for hair grow management on hairs containing little or no melanin, for example gray, white or blond hairs. The efficacy of such treatment may be enhanced by using wavelengths absorbed by melanin or by performing the treatment in conjunction with other hair removal techniques. Hypothermia may also be used to treat psoriasis, including psoriasis plaques and nail psoriasis. The teachings of this invention may thus be used to treat psoriasis, either alone or conjunction drug treatment, light treatment, for example with an excimer laser, flashlamp, uv or pulse dye laser, or other existing treatment. Scars, having different crosslinking and different denaturation thresholds then normal tissue, may be treated by hypothermia to, for example, reduce turnover, turnover being significantly enhanced for scar tissue. A special handpiece with an aperture adjustable to the shape of the scar may be desirable for treating scars. Hypothermia induced in accordance with the teachings of the invention may also be used to kill demodex mites resident in follicles which cause rosacea. Finally, hypothermia induced by this invention may be used to enhance or control growth rate of toe or finger nails or to otherwise treat conditions of these nails, for example nail fungus and dystrophic nails. The nail (matrix) is relatively accessible to light treatment. The nails can be cooled by emergence in a water bath and exposed to the light. The mechanism for enhanced nail growth may be enhanced metabolism, blood supply (vasodialation by heat and light) or biostimulation.

The application of thermal energy to tissue may also be used, for example, in physical therapy treatments, such as to enhance or accelerate wound healing or relieve pain. Beneficial effects may include a decrease in joint stiffness, an increase in joint extensibility of collagenous structures such as tendons and scar tissue, pain relief, blood-flow changes, or a decrease in muscle spasm and increase in muscle tone. As another example, large protein molecules may have high absorption coefficients, and the heating of protein-rich collagenous tissues may contribute to healing. A wide variety of conditions may be treated using this invention, for example, but not limited to, strained tendons, tenosynovitis, torn ligaments, tendonitis, bursitis, torn joint capsules, or torn muscles. As yet another example, other processes may be activated or deactivated within the tissue during heating. For example, heating of the tissue may be used to enhance or modify the activity of a pharmaceutical or another bioactive substance or to facilitate the delivery thereof through the skin. Mechanical or electrical stimulation, such as massage, may be used in conjunction with heating to achieve benefits greater then can be achieved by either alone. Pressure may also be applied to the skin surface above the treatment region to facilitate the treatment.

In another example, when tissue is heated to greater then the damage temperature of the tissue, irreversible changes to the tissue may occur, up to and including cell death, apoptosis or the like. The damage temperature is the temperature by which cells, collagen, or other tissue components may be irreversibly damaged. The damage temperature may be useful in certain therapeutic situations, for example, to damage unwanted cells or other structures, such as collagen, malignant or benign tumors, hair bulb, deep pigmented lesions or fat. Further, by heating tissue to a temperature above the body temperature (typically 37° C.), but below the damage temperature, it may be possible to change the dynamics of various biological processes, such as metabolism.

Where the tissue is a tumor, it may be desired to use heat in accordance with the teachings of this invention to kill the tumor, or at least a portion thereof, such as a necrotic center. Where the tissue is an artificially created tissue, such as a tissue-engineered scaffold, preferential heating of the center of the artificial tissue may be used, for example, to stimulate cell division within the tissue, to promote cell division or cell growth within the artificial tissue structure.

In certain embodiments, the present invention may be used for non-invasive or non-destructive reduction of localized fat deposits. For example, the invention may be used to heat fat or adipose cells past their damage temperature, causing cell damage and/or necrosis. Alternatively, the treated cells may undergo apoptosis, resulting in cell death. The dead cells may then be removed or resorbed into the body, for example, by the body's phagocytic or lymphatic systems. Fat reduction may also be achieved by heating fat or adipose cells to an elevated temperature, but below the damage temperature. For example, the fat cells may be heated to a temperature of between about 41° C. and about 45° C. Under these conditions, applying heat to subcutaneous fat may activate lipases or metabolize lipids contained within the adipose tissue found within the subcutaneous fat layer, or blood flow may increase to the heated area. Additionally, "lipolysis," or the process of breaking down fat in the body, may be regulated by enzymes sensitive to temperature, such as HSL ("hormone-sensitive lipase"). Thus, elevating the temperature of the adipose cells may increase the lipolysis rate, and thus contribute to a reduction in subdermal fat in the area being treated. This temperature can be below the temperature for vascular/lymph damage so damaged fatty cells and fatty acids can be easily removed from the treatment region. Additionally, application of the present invention may be used in combination with other fat-reduction techniques, such as medication, exercise, or adrenergic stimulation Heating of subcutaneous fat may also result in increased dermal thickness. Thus, fatty tissue may be replaced by fibrous and dermal tissue, this resulting in improved skin appearance. Thermal activation of lymph systems in subcutaneous fat can also be used to treat cellulite by removing proteins from extra cell spaces.

Stated another way, fat and/or cellulite reduction may be achieved utilizing the teachings of this invention by providing an elevated (but below damage threshold ~43-48° C.) temperature in the targeted region at depth. The mild hyperthermia initiates biological response through one or several of the following pathways:

1. Increase of activity of enzymes regulating the process of lipolysis, in particular, hormone sensitive lipase (HSL). As a result, decrease of fat stores in hypodermis.
2. Stimulation of blood and lymph flow in the targeted area with multiple positive consequences, including (but not limited to) further decrease in the fat stores and accelerated regeneration of connective tissue.
3. Induction of apoptosis in adipocytes, with subsequent removal of residual cell material by the body's scavenging system.
4. Decrease of lipid's viscosity, resulting in increasing mobility of fat globules and permeability of adipocytes' membranes.
5. Stimulation and or reorganization of the connective tissue surrounding subdermal fat depots with or without concurrent changes of the dermal collagen.

The net result is a shift of balance between fat and connective tissue in hypodermis toward the latter and improved appearance of skin.

FIG. 1 shows an apparatus 100 for one embodiment of the invention. For this apparatus, optical energy 30 from a suitable energy source 1 passes through optical (for example, focusing) device 2, filter 3, cooling mechanism 4 and contact plate 8, before reaching tissue 31. A suitable optical impedance matching lotion or other suitable substance would typically be applied between plate 8 and tissue 31 to provide enhanced optical and thermal contact. Tissue 31, as shown in FIG. 1, is divided into an upper region 5, which, for applications where radiation is applied to the skin surface, would be the epidermis and dermis, and a lower region 6 which would be a subdermal region in the previous example. Energy 30, possibly in conjunction with one or a combination of focusing from optical device 2, and wavelength selection from filter 3, and with cooling from mechanism 4, results in maximum heating occurring at a selected depth in tissue 31, which depth is, as previously indicated, at or near the junction of regions 5 and 6 or in lower region 6 for this invention. In some embodiments of the invention, certain of these components, such as, for example, filter 3 where a monochromatic source is utilized or optics 2, may not necessarily be present.

In some embodiments of the invention, energy source 1, optical device 2 and/or filter 3 may also require a cooling mechanism. This cooling mechanism may or may not be the same as or connected to cooling mechanism 4 that cools tissue 31 through contact plate 8, as indicated by arrows 32 in FIG. 1. For example, in the embodiment shown in FIG. 1, cooling mechanism 7, shown separately from cooling mechanism 4, is used to cool filter 3. Energy source 1 may be any suitable optical energy source able to produce optical energy 30 at a wavelength that produces heating within tissue 31 at the depth of a desired treatment region. The exact energy source, and the exact energy chosen, may be a function of the tissue 31 to be heated, the depth within the tissue at which treatment is desired and of the absorption of that energy in the desired area to be treated. For example, energy source 1 may be a radiant lamp, a halogen lamp, an incandescent lamp, a arc lamp, a fluorescent lamp, a light emitting diode, a laser (including diode and fiber lasers), the sun or other suitable optical energy source.

Energy source 1 may produce electromagnetic radiation, such as near infrared or visible light radiation over a broad spectrum, over a limited spectrum or at a single wavelength, such as would be produced by a light emitting diode or a laser. In certain cases, a narrow spectral source may be preferable, as the wavelength(s) produced by the energy source may be targeted towards a specific tissue type or may be adapted for reaching a selected depth. In other embodiments, a wide spectral source may be preferable, for example, in systems where the wavelength(s) to be applied to the tissue may change, for example, by applying different filters, depending on the application.

As previously indicated, in order to minimize both scattering and absorption of the applied optical radiation, the optical radiation produced by energy source 1 should be radiation with a wavelength which is minimally scattered and absorbed, the available wavelengths decreasing with increasing depth as generally indicated in Table 1.

Certain wavelengths may be preferentially absorbed by the tissue to be treated. As one example, if the tissue to be treated includes subcutaneous fat, certain wavelengths may be absorbed more effectively by the fat or adipose cells than by the surrounding tissues. For example, optical radiation having wavelengths around 925 nm, 1206 nm, 1730 nm and 2300 nm may be desirable (see for example copending application Ser. No. 09/277307, which is incorporated herein by reference, for suitable ranges); however, only the lower three of these ranges would typically provide sufficient penetration for use in practicing this invention. Using electromagnetic radiation of these wavelengths, the coefficient of absorption by this radiation in the lipids, and in particular the triglycerides located within the adipose tissue may be greater than that of the absorption coefficient of these wavelengths in water. Thus, these wavelengths when applied to a tissue sample, will preferentially be absorbed by the fat tissue, thus resulting in the preferential heating of this tissue. The selective heating of the fatty tissue can be enhanced by the lower heat capacity of fatty tissue vs. aqueous tissue. Also, the decreased blood perfusion of the subcutaneous fat vs. the dermis can be used to enhance selective heating of the fatty tissue. Compression sufficient to reduce blood flow within the target area can minimize unwanted heat convection, and therefore heat leakage, from the target area. The compression to the subdermal target area can be made selective by forming a skin fold and applying skin pressure sidewise. This results in compression of the subcutaneous fat and of skin outside the field of optical exposure. The skin on top of the skin fold, which skin is exposed to the optical radiation, is not compressed, and therefore the blood flow therein is not appreciably reduced so long as the length of the skin fold does not exceed a critical length. Blood flow within the part of the dermis exposed to optical radiation can help to remove unwanted excessive heat in this skin component.

Where optical device 2 is a focusing device, it may be any suitable device able to focus at least a portion of energy 30 arriving from energy source 1 at tissue 31, and in particular at a selected depth in tissue 31. For example, device 2 may include mirrors, prisms, reflectors, lenses such as Fresnel lenses, collimating lenses or focusing lenses, diffraction gratings, or other optical device.

Filter 3 may be any suitable filter able to select, or at least partially select, certain wavelengths or wavelength bands from energy source 1. In certain types of filters, a specific set of wavelengths may be blocked by the filter. It is also possible that undesired wavelengths in the energy from source 1 may be wavelength shifted in ways known in the art so as to enhance the energy available in the desired wavelength bands indicated above and in Table 1. Thus, filter 3 may include elements designed to absorb, reflect or alter certain wavelengths of electromagnetic radiation. For example, filter 3 may be used to remove certain types of wavelengths that are absorbed by surrounding tissues. For instance, dermis and epidermis tissues are primarily composed of water, as is much of the rest of the human body. By using a filter that selectively removes wavelengths that excite water molecules, the absorption of these wavelengths by the body may be greatly reduced, which may contribute to a reduction in the amount of heat generated by light absorption in these molecules. Thus, by passing radiation through a water-based filter, those frequencies of radiation which may excite water molecules will be absorbed in the water filter, and will not be transmitted into tissue 31. Thus, a water-based filter may be used to decrease the amount of radiation absorbed in tissue above the treatment region and converted into heat.

In other embodiments, filter 3 may be combined with other elements of the device, for example, cooling system 4 or cooling mechanism 7. Thus, water may both attenuate energy 30 arising from energy source 1, as well as cool the contact plate, and tissue in contact with the contact plate, or various other components of the device. More than one filter or filter type may also be present.

FIG. 1 shows a cooling mechanism 4 adjacent to the surface of tissue 31. Cooling mechanism 4 may be any suitable cooling mechanism able to reduce the temperature of tissue 31. Heat energy 32 may be drawn from tissue 31 across contact plate 8 into cooling mechanism 4. For example, cooling system 4 may be air or other suitable gas that is blown over contact plate 8, cooling water, or a cooling oil or other fluid. Mixtures of these substances, such as an oil and water mixture, may also be envisioned. Cooling mechanism 4 may have any suitable configuration, for example, a flat plate, a series of conducting pipes, a sheathing blanket, or a series of channels for the passage of air, or other gases, or liquid across plate 8. For example, in one embodiment, cooling system 4 may be a water-cooled contact plate. In another embodiment, cooling mechanism 4 may be a series of channels carrying a coolant fluid or a refrigerant fluid (for example, a cryogen), which channels are in contact with tissue 31 or with plate 8. In yet another embodiment, cooling system 4 may comprise a water or refrigerant fluid (for example R134A) spray, a cool air spray or air flow across the surface of tissue 31. In other embodiments, cooling may be accomplished through chemical reactions (for example, endothermic reactions), or through electronic cooling, such as Peltier cooling. In yet other embodiments, cooling mechanism 4 may have more than one type of coolant, or cooling mechanism 4 and/or contact plate 8 may be absent, for example, in embodiments where the tissue is cooled passively or directly, for example, through a cryogenic or other suitable spray. Sensors or other monitoring devices may also be embedded in cooling mechanism 4, for example, to monitor the temperature, or determine the degree of cooling required by tissue 31, and be manually or electronically controlled.

In certain cases, cooling mechanism 4 may be used to maintain the surface temperature of tissue 31 at its normal temperature, which may be, for example, 37 or 32° C., depending on the type of tissue being heated. In other embodiments, cooling mechanism 4 may be used to decrease the temperature of the surface of tissue 31 to a temperature below the normal temperature of that type of tissue. For example, cooling mechanism 4 may be able to decrease the surface temperature of tissue 31 to, for example, a range between 25° C. and −5° C.

In some embodiments of the invention, such as shown in FIG. 1, energy 30 from energy source 1 may pass through cooling mechanism 4. In these types of configurations, cooling mechanism 4 may be constructed out of materials able to transmit at least a portion of energy 30, for example, air, water or other gases or fluids, glass, or a clear plastic. In other embodiments, cooling mechanism 4 may be formed out of a series of discrete channels, and energy 30 may pass between these channels. In other embodiments of the invention, energy 30 may not be directed through cooling mechanism 4. For example, in the embodiment shown in FIG. 8, energy source 19 and cooling system 18 may be positioned on opposite sides of chamber 17.

Contact plate 8 may be made out of a suitable heat transfer material, and also, where the plate contacts tissue 31, of a material having a good optical match with the tissue. Sapphire is an example of a suitable material for plate 8. In some embodiments, contact plate 8 may have a high degree of thermal conductivity, for example, to allow cooling of the surface of the tissue by cooling mechanism 4. In other embodiments, contact plate 8 may be an integral part of cooling mechanism 4, or be absent. Contact plate 8 may be made out of a deformable or viscoelastic material in some embodiments of the invention, for example, a gel such as a hydrogel. In other embodiments, contact plate 8 may be made of a solid material, such as a glass, a crystal such as sapphire, or a plastic. In some embodiments of the invention, such as shown in FIG. 1, energy 30 from energy source 1 may pass through contact plate 8. In these configurations, contact plate 8 may be constructed out of materials able to transmit at least a portion of energy 30, for example glass, sapphire, or a clear plastic, or contact plate 8 may be constructed in such a way as to allow at least a portion of energy 30 to pass through contact plate 8, for example, via a series of holes within contact plate 8.

In certain embodiments of the invention, various components of system 100 may require cooling. For example, in the embodiment shown in FIG. 1, optical device 2 and filter 3 may be cooled by cooling mechanism 7. The design of cooling mechanism 7 may be a function of the components used in the construction of the apparatus. Cooling mechanism 7 and cooling mechanism 4, in FIG. 1, are illustrated as separate systems. However, in other embodiments, cooling mechanism 7 and cooling mechanism 4 may be part of the same system, or one or both may be absent. Cooling mechanism 7 may be any suitable cooling mechanism known in the art, such as air, water, or an oil. Mixtures of these substances, such as an oil and water mixture, may also be envisioned. Cooling of the components may be accomplished through convective or conductive cooling.

One or more of energy source 1, optical device 2, filter 3, cooling mechanism 4, or cooling mechanism 7 may be electronically controlled. For example, sensors embedded in cooling mechanism 4 or contact plate 8 may determine the amount of energy reaching tissue 31, and may direct energy source 1 to produce more or less energy or may direct cooling mechanism 4 to increase or decrease cooling, depending on the application. Other sensors and the like may be embedded in any of the components illustrated herein. The controls may be, for example, electronically preprogrammed, or manually operable.

Figure 8:
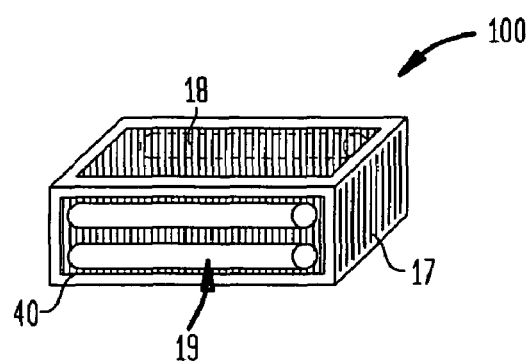
FIG. 8 is a schematic diagram of another embodiment of the invention, showing yet another internal design configuration.
Figure 9:
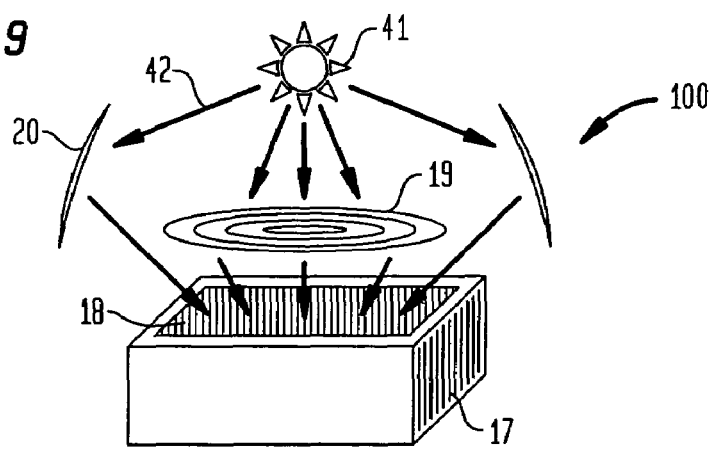
FIG. 9 is a schematic diagram of another embodiment of the invention having a different configuration.

The present invention is not limited to treating a specific region or area of tissue. For example, as illustrated in FIGS. 8 and 9, the invention may be constructed in such a way as to treat an entire person. For example, in FIG. 8, chamber 17 contains cooling mechanism 18 and energy source 19. Cooling mechanism 18 may be cooled in the same ways described above for cooling mechanisms 4 and 7. Energy source 19 may contain, for example, a series of lamps or other energy sources, optionally surrounded by filters 40. In this embodiment, filters 40 are built into the side of chamber 17. FIG. 9 shows another design, where chamber 17 has a cooling mechanism 18, but does not contain an energy source. Instead, energy 42 from the sun 41 or another energy source, such as an external lamp, is directed to chamber 17, for example, directly, by means of reflectors 20, or by means of a lens such as Fresnel lens 19. The patient may be cooled within the chamber by air flow or other suitable cooling mechanism 18.

Figure 2:
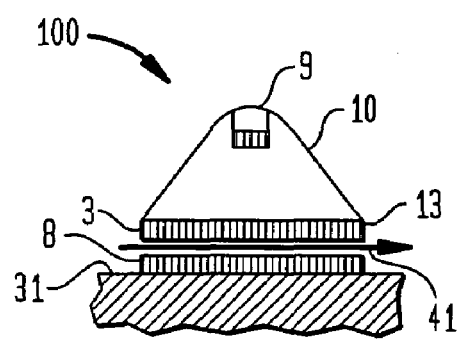
FIG. 2 is a schematic diagram of another embodiment of the invention, showing an internal design configuration.
Figure 3:
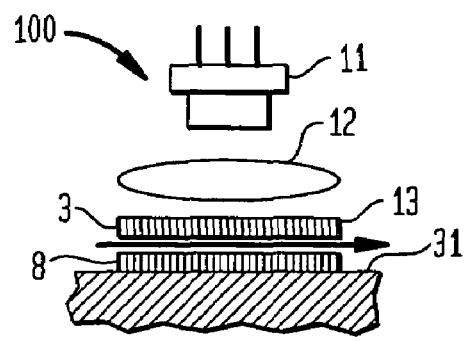
FIG. 3 is a schematic diagram of another embodiment of the invention, showing another internal design configuration.

In FIG. 2, another embodiment of the invention is shown. In this embodiment, a lamp 9, for example an incandescent lamp, is used as the energy source. Lamp 9 is surrounded by a specially coated reflector 10 to maximize light delivery efficiency to the treatment region of tissue 31. A fluid 13 may pass between contact plate 8 and filter 3. Contact plate 8, cooled by fluid 13, may cool the surface of the tissue to which it is applied. In FIG. 3, lamp 9 has been replaced by a monochromatic light emitting element 11 and lens 12, element 11 being, for example a laser diode, other suitable laser or a light emitting diode. As in the embodiment shown in FIG. 2, contact plate 8 and filter 3 are cooled by fluid 13 flowing therebetween; these two components may also be cooled by flow of cold liquid gas, for example R134A, from a pressurized can. Thus, this embodiment illustrates how a monocromatic element 11 may be used as the energy source.

Figure 4:
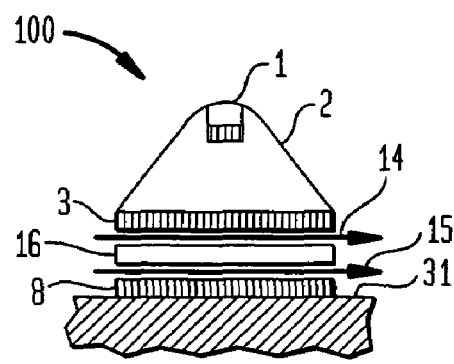
FIG. 4 is a schematic diagram of another embodiment of the invention, showing another internal design configuration.
Figure 5:
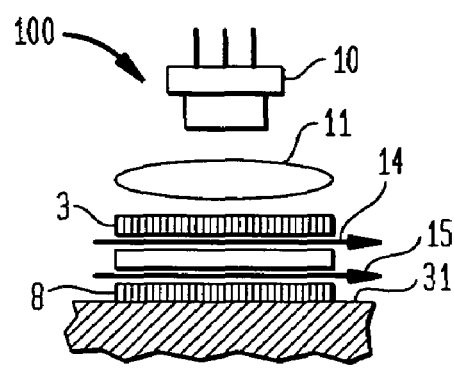
FIG. 5 is a schematic diagram of another embodiment of the invention, showing another; internal design configuration

A different type of cooling mechanism is illustrated in FIG. 4. In FIG. 4, energy arising from energy source 1 is reflected using reflector 10 through filter 3, a transparent isolating material 16, and contact plate 8. Two fluids are used to cool the filter and the contact plate. Upper fluid 14 flows between filter 3 and isolating material 16, while lower fluid 15 passes between isolating material 16 and contact plate 8. Fluids 14 and 15, in this embodiment, may not be the same fluid; however, in other embodiments, the two fluids may be the same fluid, or have a common reservoir. Contact plate 8, in this embodiment, may be made out of, for example, a transparent or a semi-transparent material, such as a glass, plastic or sapphire. Alternatively, contact plate 8 may be formed out of an opaque material, but have openings to allow energy to pass through contact plate 8. A similar embodiment of the invention is shown in FIG. 5, where the energy source 1 has been replaced by an element that produces discrete wavelengths, such as a light emitting diode or a laser diode 11. Optional lens 12 has also been added to the system as illustrated in FIG. 5.

Figure 6:
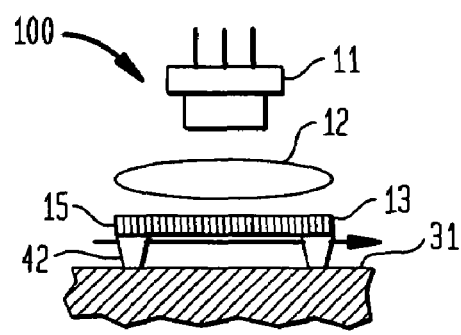
FIG. 6 is a schematic diagram of another embodiment of the invention, showing another internal design configuration.

In certain embodiments of the invention, contact plate 8 may be absent. For example, in the embodiment shown in FIG. 6, no contact plate is used, and fluid 13 (for example a liquid, gas such as air or a spray) passes or flows directly over the surface of tissue 31. Legs 42 connected to the device may be constructed in such a manner as to correctly position filter 3 over the surface of the tissue. Legs 42 may be any component able to maintain a proper distance between the surface of tissue 31 and device 100. In some embodiments of the invention, legs 42 may be constructed out of a flexible or a semi-solid substance that, for example, may conform to the surface of tissue 31, such as a gel. In other embodiments of the invention, legs 42 may be constructed out of a solid substance, such as rubber or plastic. Legs 42 may have any arrangement underneath the device that allows for the proper positioning of the device relative to the tissue. For example, legs 42 may be arranged in a triangular or a square pattern. In other embodiments of the invention, legs 42 may be a ring or a series of bars that surrounds the area being treated or legs 42 may be absent.

Figure 7:
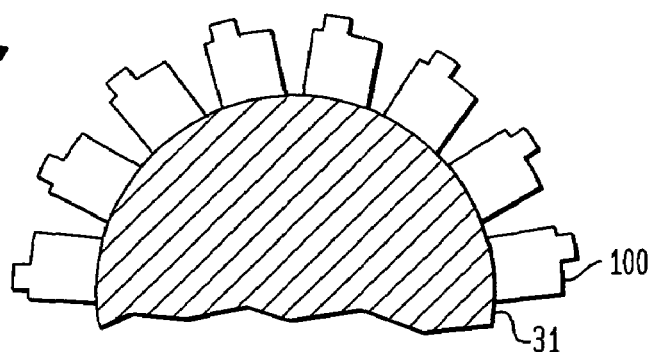
FIG. 7 is a schematic diagram illustrating a plurality of devices of the invention being used in conjunction with each other.

More than one device 100 of this invention may be used simultaneously. For example, in FIG. 7, a series of devices 100 have been arranged into a semicircular pattern. These devices may be linked together to treat large areas of a subject's body. Additionally, the devices may be interconnected in such a way as to provide flexibility, so that, for example, the apparatus may conform to the contours of the body. For example, the device may be worn as a belt, a leg wrap, an arm wrap, or wrapped around the torso. Devices 100 may also be mounted to a chair, bed or other suitable surface for the treatment of a patient's back, thighs and/or buttocks. Alternatively, devices 100 may be used to create an array of small island areas within a larger area (see for example copending application Ser. No. 10/033,302 which is incorporated herein by reference). This may, for example, be a safer alternative to large area heating, particularly for extended treatment regimens. By optimizing the spacing between treated areas, for example, through the addition of "masks" in filter 3 between energy source 1 and tissue 31 that block portions of the energy arising from energy source 1, and/or through the use of multiple separate devices 100 as is shown in FIG. 7, treatment of the subdermal tissue may be maximized, while causing a minimal amount of patient discomfort, and/or allowing faster recovery time.

Where optical source 1 is a continuous wave (CW) or other long duration source, device 100 for various of the embodiments may be slid or scanned over the surface of the patient's skin to overlie successive treatment regions, the dwell time, and thus the treatment duration, for each such region being a function of the rate at which the device is moved. The device may also include a cooling mechanism ahead of the portion of the device under source 1 to precool skin above the treatment region (see for example issued U.S. Pat. Nos. 6,273,884 and 6,511,475, which are incorporated herein by reference).

Any of the embodiments can include a contact sensor to assure good optical and thermal coupling, and systems operating in the sliding mode may also include one or more motion sensors to control radiation delivery, cooling and other functions dependent on scanning speed, to enhance system safety and for other reasons.

In addition to coupling the deep heating treatment of this invention with deep cooling to enhance treatment of fat, bone, muscle, etc., device 100 may also include a massager, vibrator or other mechanical stimulation device or a DC or other suitable electrical stimulation source. It has been found that such mechanical or electrical stimulation is more effective for hot tissue. Similarly, the effect of deep heating may be enhanced by massage or other stimulation because both heat and cold generally penetrates better in compressed skin and subdermal tissue. Thus, the combination of deep heating and mechanical or electrical stimulation may provide significantly better results then either one alone. Heating may also be enhanced by supplementing the optical heating with, for example electro-stimulation by AC/DC, or additional heating by RF, etc. Tensioning or pressure applied to the skin overlying the treatment region may also enhance treatment effect.

The teachings of this invention may also be utilized for hair removal treatments by targeting the hair bulb, which is generally located in the subcutaneous layer 6. The treatment would be done at low power sufficient to raise the temperature of the fat surrounding the hair bulb, and thus the hair bulb, to roughly 45° C. and should be performed for a relatively long time period, for example, 15 minutes. The hair bulb also contains high proliferation water cells which react strongly with the applied radiation to increase bulb temperature, leading to the destruction thereof.

The function and advantages of these and other embodiments of the present invention will be more fully understood from the following examples. These examples are intended to be only illustrative in nature and are not intended to limit the scope of the invention.

EXAMPLE 1

This example illustrates theoretical calculations corresponding to one embodiment of the invention as applied to human skin.

Figure 10:
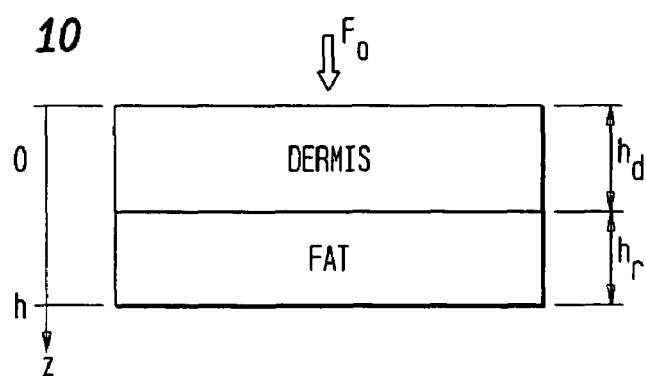
FIG. 10 is a schematic drawing of a model of tissue, used in certain calculations.

Initially, a model of the skin was prepared. This model included two layers of tissue possessing distinct optical and thermal properties: dermis and subcutaneous fat (FIG. 10). The presence of fine structures such as the basal layer and the vessel plexus was neglected. Monochromatic light was assumed to be incident normal to the surface. The input power density was designated as $F_0$. Both the surface temperature ($T_s$) at depth z=0 and the bottom temperature ($T_h$) at depth z=h were kept fixed at prescribed levels. Specifically, $T_h$ was set at 37° C. due to the temperature stabilization effect of blood and metabolic heat generation on muscle tissue. The objective of this example was to evaluate the steady-state temperature distribution within the skin and to find the characteristic depth $z_{max}$ where the steady-state temperature reaches a maximum.

Starting with the problem of light transport within the tissue, scattering in both tissue layers predominated strongly over absorption, allowing the diffuse approximation to be applied. This approach was particularly valid within the wavelength range of 600 min to 1400 nm, which may also be referred to as the "therapeutic window". The one-dimensional light transport problem in the diffusion approximation for the two-layered tissue model of FIG. 10 can be solved assuming both the tissue irradiance and the light flux to be the continuous functions of coordinate z at the dermis and fat interface. The resulting expression for the tissue irradiance, $\psi$, obtained may be written in the following general form:

$$\psi_1(z) = F_0 \tau_{col} \cdot [V_1 \cdot \exp(-\kappa_1 \cdot z) + V_2 \cdot \exp(\kappa_1 \cdot z) - V_3 \cdot \exp(-\mu t_1 \cdot z)], \quad z \leq h_d$$

$$\psi_2(z) = F_0 \tau_{col} [V_4 \cdot \exp(-\kappa_2 \cdot (z - h_d)) - V_5 \cdot \exp(-\mu t_2 \cdot (z - h_d))], \quad z > h_d \quad (1)$$

where indices 1 and 2 stand for dermis and subcutaneous fat, respectively. $\kappa = \sqrt{3 \cdot \mu_a \cdot \mu_{tr}}$ and $\mu t = \mu_a + \mu_s$, are the diffusion and extinction coefficients for light in the corresponding layers, and $$\tau_{col} = \frac{4 n_1 n_2}{(n_1 + n_2)^2}$$

is the attenuation coefficient of the collimated light at the surface.

Flux amplitudes $V_1$ to $V_5$ were determined by the boundary and interface conditions. In particular, if the coefficients of refraction of both layers are the same, the interface condition at $z = h_d$ is such that both the radiance and the total light flux should be continuous functions of depth.

Turning to the problem of heat conduction within the two-layered tissue model, the time dependent equation of heat conduction in the k-th layer was:

$$\frac{\partial}{\partial t} T(z, t) = \alpha_k \frac{\partial^2}{\partial z^2} T(z, t) + Q_k(z, t), \quad (2)$$

yielding the following steady-state equation:

$$\alpha_k \frac{d^2}{d z^2} T(z) = -Q_k(z), \quad (3)$$

where $\alpha_k$ was the thermal diffusivity of the k-th layer (k=1,2). The heat source term $Q_k$ in these equations describes the generation of heat due to light absorption in the tissue. In the steady-state case, the source term is:

$$Q_k(z) = \frac{\mu_{ak}}{\rho_k \cdot c_k} \cdot \psi_k(z), \quad (4)$$

where $\mu_{ak}$, $\rho_k$ and $c_k$ are the coefficient of absorption, density, and specific heat of the k-th layer, respectively.

Boundary conditions were assumed to be $T(0)=T_s$, $T(h)=T_h$. The solution of Equation (3) was then found to be:

$$T_2(z) = T_h + B \cdot (h - z) - \frac{1}{\alpha_2} \cdot \int_z^h dz' \int_{hd}^{z'} dz'' Q(z''), \quad (5)$$

$$T_1(z) = T_s + A \cdot z - \frac{1}{\alpha_1} \cdot \int_0^z dz' \int_0^{z'} dz'' Q(z''),$$

where parameters A and B have to be found from the interface conditions. For the case of perfect thermal contact:

$$T_1(h_d) = T_2(h_d), \quad (6)$$

$$k_1 \frac{d}{dz} T_1(h_d) = k_2 \frac{d}{dz} T_2(h_d),$$

where and $k_1$ and $k_2$ are the thermal conductivities of dermis and fat, respectively.

The analytic expression for the temperature, T(z), was then obtained by substituting Equation (3) into Equations (4) and (5).

A simpler expression for the temperature distribution was obtained for a homogenous medium with no layered structure. In this case, the radiance distribution took the following general form:

$$\psi(z) = F_0 \tau_{col} [\exp(-\mu_t z) + \phi_d(z)], \quad (7)$$

where the first term was the collimated radiance and the second one was the diffuse radiance given by:

$$\phi_d(z) = V_2 \cdot \exp(-\kappa \cdot z) - V_1 \cdot \exp(-\mu_t z) \quad (8)$$

The temperature distribution was:

$$T(z) = \quad (9)$$

$$T_s + (T_h - T_s) \cdot \frac{z}{h} + F_0 \frac{V_0}{\alpha} \left\{ \frac{1 - V_1}{\mu_t^2} \cdot \left[ 1 - e^{-\mu_t z} - (1 - e^{-\mu_t z}) \cdot \frac{z}{h} \right] + \frac{V_2}{\kappa^2} \cdot \left[ 1 - e^{-\kappa \cdot h} - (1 - e^{-\kappa \cdot h}) \cdot \frac{z}{h} \right] \right\} \text{ with } V_0 = \mu_a \cdot \tau_{sp} / (\rho c).$$

Differentiating Equation (9) with respect to z yields the following implicit expression for the depth zmax, the localized tissue depth at which maximum temperature occurs:

$$T_h - T_s = \frac{F_0 \cdot V_0}{\alpha} \cdot \left[ \frac{1 - V_1}{\mu_t^2} \cdot (1 - e^{-\mu_t h} - \mu_t \cdot h \cdot e^{-\mu_t z_{max}}) + \frac{V_2}{\kappa^2} \cdot (1 - e^{-\kappa \cdot h} - k \cdot h \cdot e^{-\kappa z_{max}}) \right] \quad (10)$$

Tmax=Th−Ts is maximum temperature rise in the tissue at the depth zmax.

Equation (10) was solved numerically. To get an approximate analytic expression, the inequality $\mu_1 >> \kappa$ was used, which is typically valid within the therapeutic window. Then, dropping the exponential terms with $\mu_t$, and solving the simplified equation with respect to $z_{max}$ yielded the following $$z_{max} = -\frac{1}{\kappa} \cdot \ln \left[ \frac{\kappa \cdot (1 - V_1)}{V_2 \cdot h \cdot \mu_t^2} + \frac{1 - \exp(-\kappa h)}{\kappa h} - \frac{\alpha \kappa}{F_0 V_0 V_2 h} \cdot (T_h - T_s) \right]. \quad (11)$$

Maximum temperature can be calculated from (9) as $T_{max} = T(z_{max})$

Figure 11:
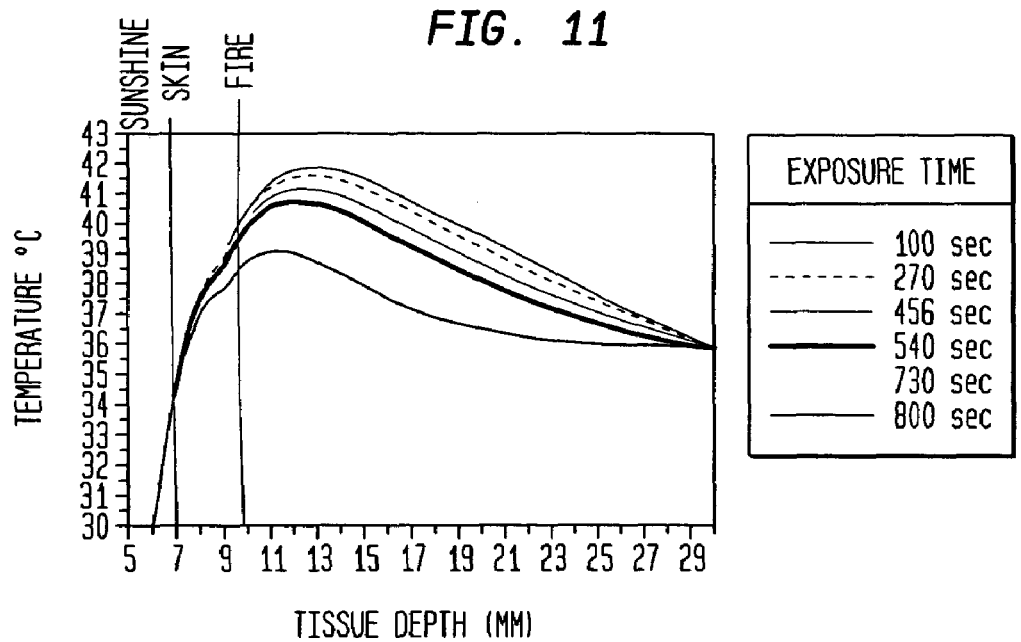
FIG. 11 is a plot of the temperature produced by an embodiment of the invention in a tissue sample versus tissue depth.
Figure 13:
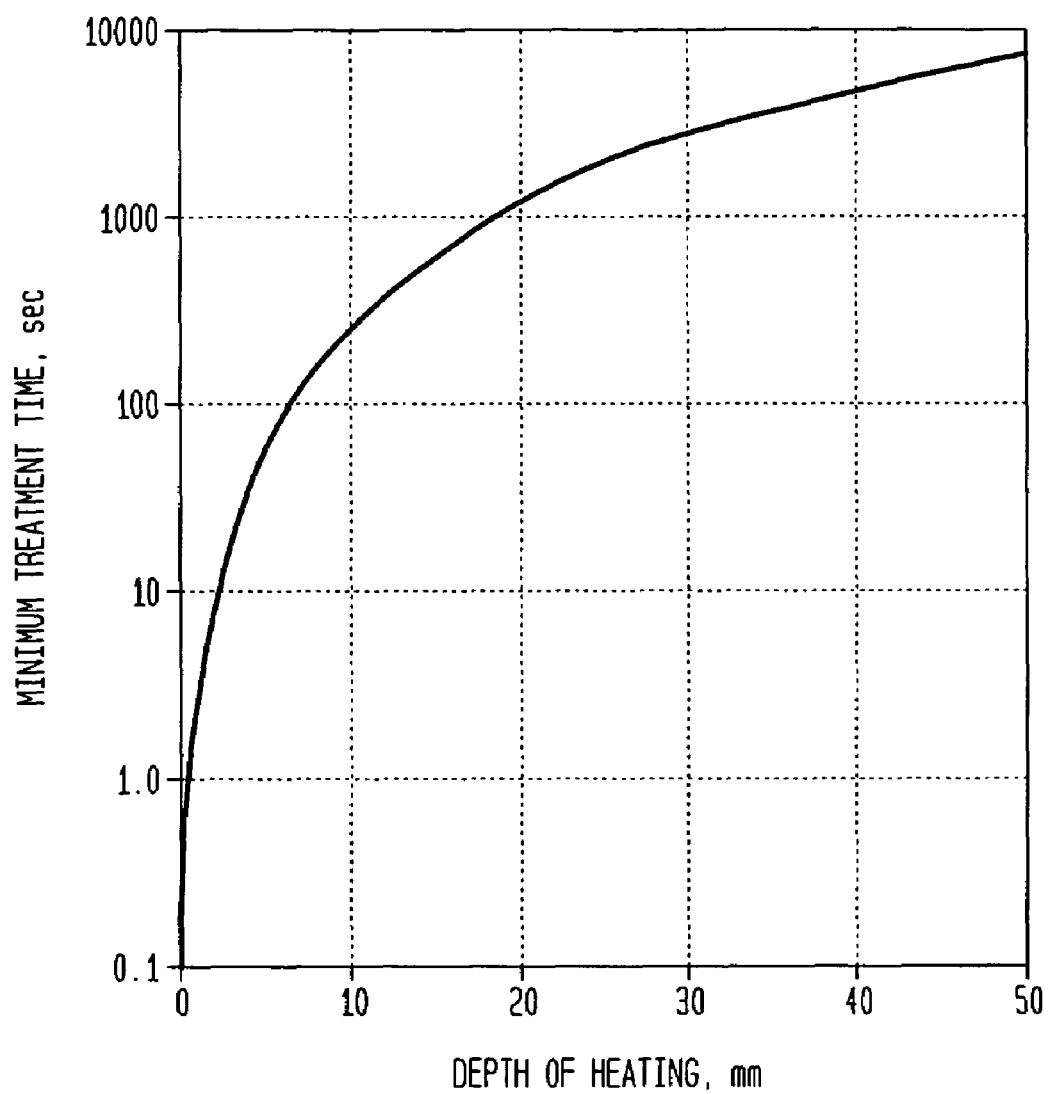
FIG. 13 is a plot of depth of heating vs. treatment time as determined using Equation 12.

It can be seen from these results that an increase in $F_0$ caused the temperature maximum to move upwards, provided the input flux is sufficiently small. At larger value of $F_0$, the maximum ceased to move while proceeding to grow in amplitude. The treatment time should be long enough to remove heat from the layer $0<z<z_{max}$. This time $t_{min}$ was given by the formula:

$$t_{min} = \frac{(6 \div 60) \cdot z_{max}^3}{\alpha_1 \cdot z_1 + \alpha_2 \cdot z_2} \quad (12)$$

where $z_1$ is the depth into dermis and $z_2$ is depth into subcutaneous fat, and $z_1+z_2=z$ is depth of treatment. The numerator constant $(6\div60)$ varies within the given range depending on how close the desired temperature is to Tmax, being 6 for Tzmax=90% Tmax and 60 for Tzmax=99% Tmax. The treatment time must be longer than $t_{min}$. FIG. 11 shows a typical temperature distribution in the body. FIG. 13 and Table 2 show minimum treatment time as a function of depth of treatment z.

Equations (10), (11), and (12) describe a set of heating and cooling parameters that allow control of both the value and location of the internal temperature maximum. FIG. 11 shows a graph generated using these equations that shows that a broad spectral source, having a proper set of filters, combined with surface cooling, allows the temperature within the adipose layer of tissue to be elevated to a maximum, while maintaining acceptable temperatures surrounding tissue and in particular, in tissue above the treatment region through which the radiation passes.

Thus, this example illustrates theoretical calculations corresponding to one embodiment of the invention.

EXAMPLE 2

The following prophetic example illustrates treatment parameters for different body layers that may be used in one embodiment of the invention, as applied to human skin.

Based on the calculation illustrated in Example 1, treatment parameters for different layers of the body that may be used in one embodiment of the invention can be determined. These calculations are summarized in Table 1. The body layers model includes the reticular dermis, dermis subcutaneous fat junction, and subcutaneous fat layer.

Using a broad-spectrum lamp in this embodiment of the invention, the treatment parameters include a surface cooling mechanism able to maintain a surface cooling temperature of between 0° C. and 32° C.; a broad-spectrum lamp, where the color temperature of the lamp is between 300 K and 3000 K, with filtering of more than 50% of the light having wavelengths of less than 800 nm and greater that 1800 nm, preferably 900 to 1400 nm, and most preferably 1100 to 1250 nm. Depending on depth, the treatment being performed and other factors, the power may vary from approximately 0.2 to 50 W/cm2, and more preferably from approximately 0.5 to 20 W/cm2, with a treatment time of between 2 sec for a 1 mm depth and 7300 sec for a 50 mm depth When operating in sliding mode, treatment power and duration increase.

Thus, this prophetic example illustrates exemplary treatment parameters that may be used to heat different layers of the body, in one embodiment of the invention.

TABLE 1

Typical parameters of treatment:

| Organ | Depth of peak temperature, mm | Wavelength range, μm | | | Treatment parameters with precooling for preferable wavelength range | | | | |
|---|---|---|---|---|---|---|---|---|---|
| | | Maximum | Preferable | Most preferable | Cooling temperature, ° C. | Precooling time, s | Time of treatment, s | Fluence J/cm² | W/cm² |
| Reticular dermis | 1-3 | 0.6-1.85 | 0.8-1.4 & 1.5-1.8 | 1.2-1.3 & 1.6-1.8 | 5 | 1-30 | 2-40 | 10-200 | 5-30 |
| Dermis subcutaneous fat junction | 2-5 | 0.6-1.35 & 1.6-1.8 | 1.1-1.25 & 1.65-1.8 | 1.15-1.23 & 1.7-1.75 | 5 | 1-30 | 10-40 | 150-200 | 5-15 |
| Subcutaneous fat | 5-10 | 0.8-1.4 & 1.6-1.7 | 1.1-1.3 & 1.65-1.8 | 1.15-1.23 | 5 | 30-110 | 40-300 | 200-500 | 1.7-5 |
| | 10-20 | 0.8-1.3 | 1.1-1.25 | 1.15-1.23 | | 110-450 | 300-800 | 500-1000 | 1.2-5 |
| | 20-50 | 0.8-1.3 | 1.05-1.25 | 1.05-1.15 | | 450-2800 | 800-1200 | 1000-1200 | 1-1.2 |

| Organ | Treatment parameters without precooling for preferable wavelength range | | |
|---|---|---|---|
| | Cooling temperature, ° C. | Minimum time of treatment, s | Power density, W/cm² |
| Reticular dermis | 5 | 2-65 | 2.5-50 |
| Dermis subcutaneous fat junction | 5 | 2-65 | 2.5-50 |
| Subcutaneoucs fat | 5 | 65-270 | 0.5-20 |
| | | 270-1100 | |
| | 5 | 1100-7300 | 0.5-10 |
| | 5 | | 0.2-5 |

TABLE 2

Minimum treatment time without precooling

| Depth, mm | Treatment time, sec |
|---|---|
| 1 | 2 |
| 2 | 10 |
| 3 | 20 |
| 4 | 40 |
| 5 | 65 |
| 6 | 95 |
| 7 | 130 |
| 8 | 170 |
| 9 | 220 |
| 10 | 275 |
| 12 | 400 |
| 14 | 550 |
| 16 | 720 |
| 18 | 915 |
| 20 | 1100 |
| 25 | 1800 |
| 30 | 2600 |
| 35 | 3500 |
| 40 | 4600 |
| 45 | 5900 |
| 50 | 7300 |

EXAMPLE 3

Figure 12:
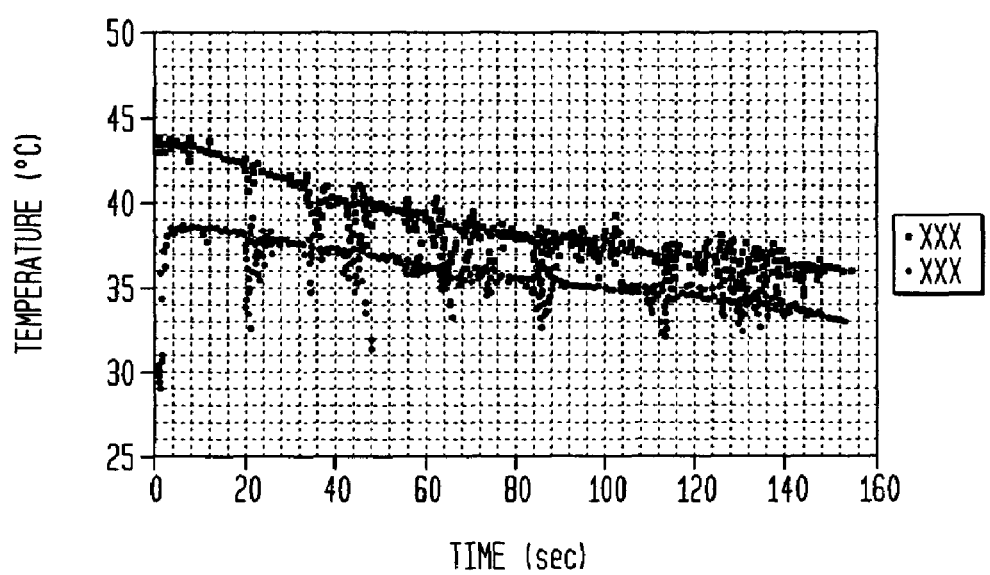
FIG. 12 is a plot of a temperature relaxation profile produced by an embodiment of the invention in a tissue.

In this example, a device 100 of this invention substantially as shown in FIG. 2 was used to heat subcutaneous fat in the stomach region of a volunteer. Light from a halogen lamp 9 was filtered with a combination of a short cut or high pass filter 8 with an 800 nm cut-off and a 3 mm thick water layer 41. The temperature of water 41 was 12° C., while the temperature of a sapphire plate 8 and of the skin interface was 18° C. Power density was 4 W/cm2 and the treatment time was 300 sec. After heating the subcutaneous fat layer for 300 sec., the device was removed, and two thermocouples were immediately implanted 1 mm and 8 mm below the skin surface under the heated region to determine the final, steady-state temperatures and to monitor the temperature relaxation profiles in the dermis and fat layer respectively. Temperature data recorded by the two thermocouples are shown in FIG. 12. The initial temperatures of the subcutaneous fat layer at a depth of 8 mm was found to be approximately 45° C., while the temperature of the dermis, 1 mm below the surface of the skin, was found to be about 40° C. and the temperature at the epidermis was 24° C. Over the course of the next several minutes, the temperatures of the dermis and the subcutaneous fat layer decreased towards basal levels of 37° C. for the subcutaneous fat layer and approximately 32° C. for the dermis.

The same device 100 was used to perform the same test on a 25 mm bulk of pig skin and subcutaneous fat which was placed on a thermally stable plate with a temperature of 37° C. The power density for this test was 10 W/cm2 and cooling water having a temperature of 4° C. was used. After a treatment time of 300 sec., peak temperature of 53° C. was found at a depth 14 mm into the fat. The temperature at the epidermis at this time was 38° C. After about 6 weeks, this exposure setting induced reduction of subcutaneous fat without evidence for epidermal damage. A partial replacement of fatty tissue by connective collagen tissue was observed. A reduction of hair growth was also observed several weeks after this and similar exposure settings, even if a lower temperature rise was obtained and only a single treatment was performed. This clearly emphasized the possibility of using this method to manage unwanted hair growth. Highly proliferating cells like sebocytes within the sebaceous glands or hair matrix cells within the hair follicle are particularly sensitive to heating which can be used to achieve selective effects on these structures even by unselective heating of the depth were these structures are located. Hair matrix cells are also surrounded by fatty cells and the sebaceous glands are generating lipids. The decreased heat capacity for lipids provides additional selective effects. This can also be specifically useful for the treatment of non pigmented hairs that are usually not affected by standard light assisted methods for photoepilation based on selective photothermolysis. Hair growth management may include permanent or temporary hair removal or merely controlling/slowing hair growth rate.

These examples thus illustrates how a device of the invention may be used to heat a subdermal layer of tissue to a temperature significantly higher than normal body temperature and the temperature of surrounding tissue, including tissue between the skin surface and the treatment region.

While several embodiments of the invention have been described and illustrated herein, those of ordinary skill in the art will readily envision a variety of other means and structures for performing the functions and/or obtaining the results and/or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention. In the claims, all transitional phrases or phrases of inclusion, such as "comprising," "carrying," "having," "containing," and the like are to be understood to be open-ended, i.e. to mean "including but not limited to." Only the transitional phrases or phrases of inclusion "consisting of" and "consisting essentially of" are to be interpreted as closed or semi-closed phrases, respectively.

What is claimed is:

1. Apparatus for treating at least a selected region at depth of a patient while protecting tissue above the selected region, comprising:

an optical radiation source for delivering optical radiation at a power of between 0.2-50 W/cm$^2$ to the patient's skin, said optical radiation being applied to said selected region for at least approximately 2 seconds;

wherein said source includes a broadband optical radiation source, and a filter through which radiation from said broadband source is passed;

wherein said filter includes a water filter to at least attenuate wavelengths from said broadband source which are selectively absorbed by water; and a cooling mechanism for cooling tissue above said selected region to a temperature below that of said selected region.

2. Apparatus as claimed in claim 1 wherein said water filter includes chilled water flowing between said broadband source and the patient's body, said flowing chilled water also functioning as part of said mechanism for cooling.

3. Apparatus as claimed in claim 1 wherein said cooling mechanism also cools said filter.

4. Apparatus as claimed in claim 1 including a mechanism for removing heat from said filter.

5. Apparatus as claimed in claim 1 wherein said source includes adjustable optics for shaping radiation to be delivered to said selected region.

6. Apparatus as claimed in claim 1 wherein said source is at least primarily at one or more wavelengths between about 600 nm and about 1850 nm.

7. Apparatus as claimed in claim 6 wherein said source is at least primarily at one or more wavelengths between about 800 nm and about 1350 nm.

8. Apparatus as claimed in claim 6 wherein said source is at least primarily at one or more wavelengths between about 1050 nm and about 1250 nm.

9. Apparatus as claimed in claim 1 wherein said optical radiation source and said mechanism are concurrently operated for a period of at least two seconds.

10. Apparatus as claimed in claim 9 wherein said optical radiation source and said mechanism are concurrently operated for a period of at least five seconds.

11. Apparatus as claimed in claim 9 including a precooling mechanism which cools tissue above said selected region prior to the concurrent operation of said source and said cooling mechanism.

12. Apparatus as claimed in claim 11 wherein said cooling mechanism and said precooling mechanism are the same mechanism.

13. Apparatus as claimed in claim 11 wherein said optical radiation power and said period of concurrent operation vary dependent on whether said precooling mechanism is operated.

14. Apparatus as claimed in claim 1 wherein said optical radiation source and said mechanism are concurrently operated for a period of between about two seconds and two hours.

15. Apparatus as claimed in claim 1 wherein at least 50% of the filtered light having wavelengths between 900 nm and 1400 nm such that said apparatus is an apparatus for fat reduction, said radiation heating subdermal fat tissue.

16. Apparatus as claimed in claim 1 including a mechanism for stimulating tissue in said selected region.

17. Apparatus as claimed in claim 16 wherein said mechanism for providing stimulation is at least one of a mechanical stimulator, acoustic stimulator and an electrical stimulator.

18. Apparatus as claimed in claim 1 wherein said selected region contains at least one hair bulb, wherein parameters for said apparatus, including said source, are selected to slowly damage said bulb, and wherein the treatment time for the apparatus is approximately 15 minutes.

19. The apparatus of claim 1, wherein the optical radiation source is capable of delivering radiation at a power of between 0.2-5 W/cm² to the patient's skin for a duration between two seconds and two hours, both said power and said duration increasing with increased depth for said selected regions.

20. The apparatus of claim 1, wherein the optical radiation source is capable of delivering radiation of a wavelength between 600 nm and 1850 nm and at a power of between 0.2-5W/cm² to the patient's skin, the wavelength and the power both varying as a function of the depth of the selected region.

21. The apparatus of claim 1, wherein the optical radiation source is capable of delivering radiation of a wavelength between about 600 nm and about 1850 nm, at a power of between 0.2-5 W/cm² to the patient's skin for a duration between two seconds and two hours, the wavelength, duration and power all varying as a function of the depth of the selected region.

22. Apparatus as claimed in claim 1 wherein said filtered radiation is at least primarily at one or more wavelengths between about 600 nm and about 1850 nm.

23. Apparatus as claimed in claim 1 wherein said filtered radiation is at least primarily at one or more wavelengths between about 800 nm and about 1350 nm.

24. Apparatus as claimed in claim 1 wherein said filtered radiation is at least primarily at one or more wavelengths between about 1050 nm and about 1250 nm.

25. Apparatus for treating at least a selected region at depth of a patient while protecting tissue above the selected region, comprising:
   an optical radiation source for delivering optical radiation at a power of between 0.2-50 W/cm² to the patient's skin, said power varying at least in part as a function of the depth of said selected region, said optical radiation being applied to said selected region for at least approximately 2 seconds;
   a cooling mechanism for cooling tissue above said selected region to a temperature below that of said selected region; and
   wherein parameters for said optical radiation source and for said cooling mechanism are selected to achieve a selected temperature as indicated by equation 10 at a selected depth z max determined by equation 11.

26. Apparatus as claimed in claim 25 wherein the minimum treatment time for the apparatus is determined in accordance with equation 12.

27. A method of fat reduction for treating at least a selected region at depth of a patient's body while protecting tissue above the selected region, comprising:
   (a) selectively delivering optical radiation at a power between approximately 0.2 and 5 W/cm² to the patient's body above said selected region, said optical radiation being applied to said selected region for at least approximately 2 seconds; and
   (b) concurrently cooling patient tissue above said selected region to a temperature below that of the selected region, wherein said radiation heats subdermal fat tissue.

28. A method as claimed in claim 27 wherein said power is 0.5-5 W/cm².

29. A method as claimed in claim 27 wherein step (a) includes generating broad band optical radiation, and filtering said broad band radiation before delivering it to said patient's body.

30. The method of claim 27, wherein the optical radiation is at least primarily at one or more wavelengths between about 600 nm and about 1850 nm.

31. The method of claim 30, wherein the optical radiation is at least primarily at one or more wavelengths between about 800 nm and about 1350 nm.

32. The method of claim 30 wherein the electromagnetic energy is at least primarily at one or more wavelengths between about 1050 nm and about 1250 nm.

33. The method of claim 27 wherein step (a) and step (b) are performed concurrently for a period of at least two seconds.

34. The method of claim 33 wherein step (a) and step (b) are performed concurrently for a period of at least five seconds.

35. The method of claim 27 wherein step (a) and step (b) are performed concurrently for a period of between about two seconds and about two hours.

36. The method of claim 27 including the step of precooling tissue above said selected region.

37. The method of claim 27 wherein said method is a method for fat reduction, subdermal fat tissue being heated during step (a).

38. The method of claim 27 including the step of stimulating tissue in said selected region.

39. The method of claim 38 wherein said step of providing stimulation provides at least one of mechanical stimulation, acoustic stimulation and electrical stimulation.

40. A method for treating at least a selected region at depth of a patient's body while Protecting tissue above the selected region, comprising:

precooling tissue above said selected region;

selectively delivering optical radiation at a power between approximately 0.2 and 5 W/cm² to the patient's body above said selected region, said optical radiation being applied to said selected region for at least approximately 2 seconds; and concurrently cooling patient tissue above said selected region to a temperature below that of the selected region, The method of claim 38 wherein said optical radiation power and said period of concurrent operation vary dependent on whether said precooling step is performed.

41. The method of claim 40 wherein said selected region is heated during the step of selectively delivering optical radiation.

42. The method of claim 40, wherein step of selectively delivering radiation at a power between approximately 0.2 and 5 W/cm² to the patient's body above said selected region further comprises delivering said radiation for a duration of two seconds to two hours, both said power and said duration varying with the depth of said selected region; and cooling step further comprises maintaining a surface temperature below 32° C.

43. The method of claim 40, wherein the step of selectively delivering radiation further comprises delivering a wavelength between about 600 nm and about 1850 nm such that both said power and wavelength varying as a function of the depth of said selected region.

44. The method of claim 40, wherein said radiation being selected so as not to be scattered or absorbed by tissue above said selected region sufficiently to prevent sufficient radiation from reaching the selected region to effect a desired treatment.

45. A method as claimed in claim 44 wherein said selected region contains subdermal fat; and wherein said radiation at least includes at least one wavelength selectively absorbed by fat.

46. A method for treating at least a selected region at depth of a patient's body while protecting tissue above the selected region, comprising:

(a) selectively delivering optical radiation at a power between approximately 0.2 and 50 W/cm² to the patient's body above said selected region, said power varying at least in part as a function of the depth of said selected region, said optical radiation being applied to said selected region for at least approximately 2 seconds;

(b) concurrently cooling patient tissue above said selected region to a temperature below that of the selected region; and wherein parameters for said optical radiation and for said cooling are selected to achieve a selected temperature as indicated by equation 10 at a selected depth z max determined by equation 11.

47. The method of claim 46 wherein the minimum treatment time for the method is determined in accordance with equation 12.

* * * * *

UNITED STATES PATENT AND TRADEMARK OFFICE
CERTIFICATE OF CORRECTION

PATENT NO. : 7,351,252 B2  Page 1 of 1
APPLICATION NO. : 10/465137
DATED : April 1, 2008
INVENTOR(S) : Gregory B. Altshuler et al.

It is certified that error appears in the above-identified patent and that said Letters Patent is hereby corrected as shown below:

In the Claims:

At column 19, line 64, in claim 19, change "regions" to region.

At column 20, lines 65-66, in claim 32, change "electromagnetic energy" to optical radiation.

At column 21, line 21, in claim 40, change "Protecting" to protecting.

At column 21, line 31, in claim 40, delete "The method of claim 38".

Signed and Sealed this

Thirteenth Day of January, 2009

JON W. DUDAS
*Director of the United States Patent and Trademark Office*

UNITED STATES PATENT AND TRADEMARK OFFICE
CERTIFICATE OF CORRECTION

PATENT NO. : 7,351,252 B2  Page 1 of 1
APPLICATION NO. : 10/465137
DATED : April 1, 2008
INVENTOR(S) : Gregory B. Altshuler et al.

It is certified that error appears in the above-identified patent and that said Letters Patent is hereby corrected as shown below:

On the Title page item [73]

Assignee: Palomar Medical Technologies, Inc., Burlington, MA (US)

should read:

Palomar Medical Technologies, Inc., Burlington, MA (US);
The General Hospital Corporation, Boston, MA (US)

Signed and Sealed this
Fifteenth Day of April, 2014

Michelle K. Lee
*Deputy Director of the United States Patent and Trademark Office*